United States Patent [19]

Chen

[11] 4,118,431
[45] Oct. 3, 1978

[54] CONVERSION OF OXYGENATED COMPOUNDS

[75] Inventor: Nai Yuen Chen, Titusville, N.J.

[73] Assignee: Mobil Oil Corporation, New York, N.Y.

[21] Appl. No.: 734,481

[22] Filed: Oct. 21, 1976

[51] Int. Cl.² ............................................. C07C 5/00
[52] U.S. Cl. .............................. 260/668 R; 208/164;
208/143; 208/126; 208/157; 208/DIG. 2
[58] Field of Search ............... 208/164, 143, 126, 157;
260/668 R

[56] References Cited

U.S. PATENT DOCUMENTS

| 2,859,171 | 11/1958 | Fahnestock et al. | 208/126 |
| 3,151,060 | 9/1964 | Garbo | 208/143 |
| 3,894,107 | 7/1975 | Butler et al. | 260/668 R |
| 3,926,783 | 12/1975 | Wolk | 208/157 |

*Primary Examiner*—Veronica O'Keefe
*Attorney, Agent, or Firm*—Charles A. Huggett; Carl D. Farnsworth

[57] ABSTRACT

A method and system is described for effecting chemical reactions of aliphatic hetero compounds to gasoline boiling components with crystalline zeolites in the presence of a relatively inert particle material arranged to exercise distribution of exothermic heat and utilized in a catalyst system under conditions to minimize undesired deactivation of catalyst particles.

9 Claims, 2 Drawing Figures

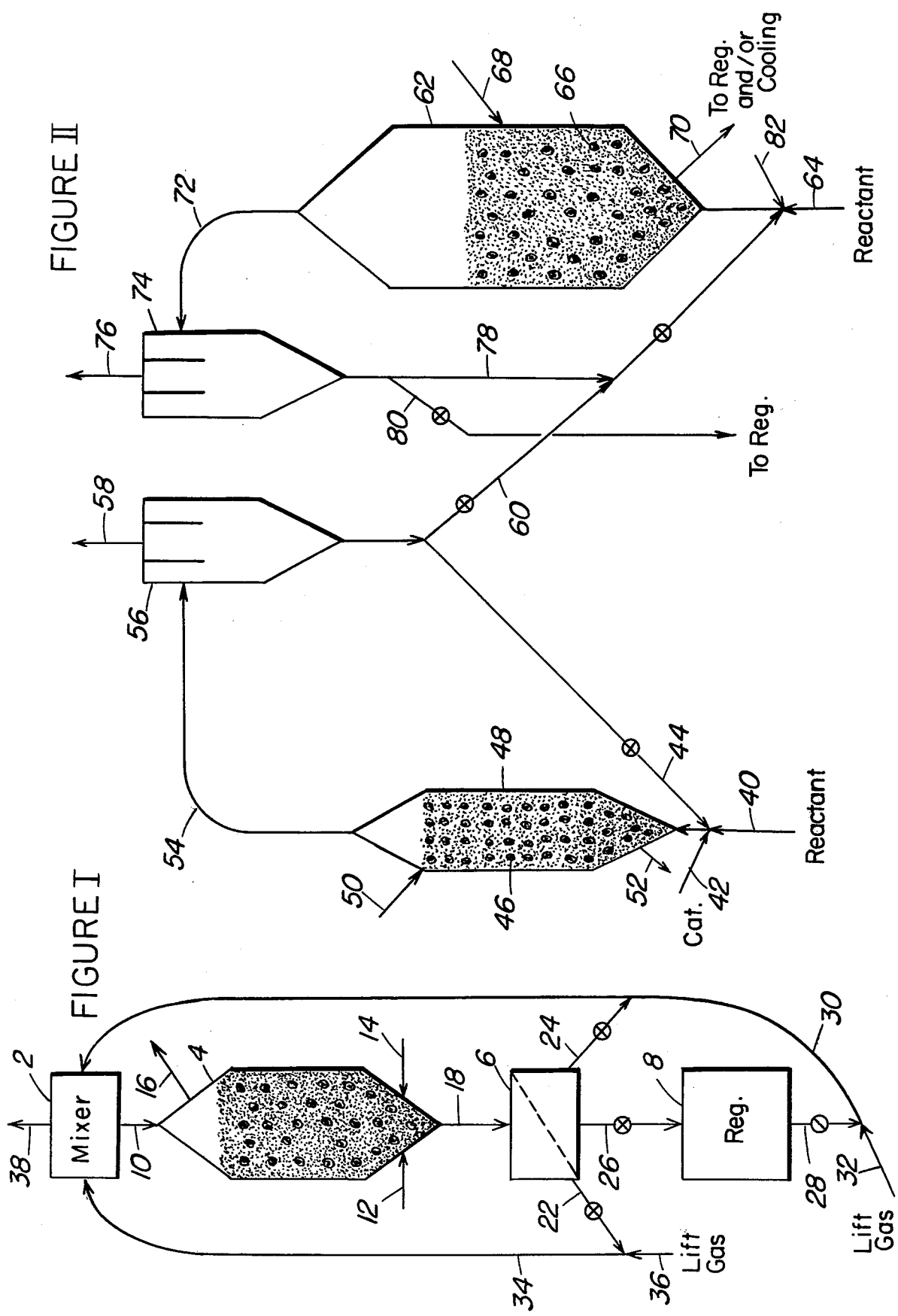

CONVERSION OF OXYGENATED COMPOUNDS

BACKGROUND OF THE INVENTION

The application of fluidized-catalyst techniques developed particularly in the petroleum industry for effecting chemical reaction embodying the distribution of heat and/or the disposal of undesired heat has long been accepted as a major processing tool of the industry. For example, the catalytic cracking of oil vapors to produce lower boiling desired products and regeneration of the catalyst used in such an operation has been particularly useful of fluidized catalyst techniques. It has also been proposed to use the fluidized catalyst technique in the highly exothermic reactions of Fischer-Tropsch synthesis and the known Oxo process primarily for the disposal of generated heat. In many of the fluidized catalyst operations developed, disposal of the reaction heat has been accomplished by many different techniques including transfer of catalyst through cooling sections and/or including indirect cooling means with a fluid bed of catalyst to absorb reaction heat transferred by the finely divided fluidized catalyst particles. Not only is the fluidized catalyst technique used for temperature control by addition and/or removal but it has also been found useful for extending the active life of the catalyst used in the process.

The present invention is concerned with an arrangement and method of operation for disposing of generated exothermic reaction heat within limits which will particularly protect and prolong the useful life of the catalyst employed in the operation.

SUMMARY OF THE INVENTION

The present invention relates to a method and arrangement of apparatus for converting aliphatic heterocompounds and derivatives thereof to gasoline boiling components in a catalyst system more efficiently utilizing the activity of the conversion catalyst. In a more particular aspect, the invention relates to discrete catalyst particle systems maintained in the presence of discrete relatively inert solid thermophore particle material of the same size, smaller or larger in size ratioed with respect to the catalytic material as a function of the catalyst activity to achieve a desired heat distribution during restructuring of the reactant feed to gasoline boiling components.

The relatively inert solid thermophore particle material employed in admixture with catalyst particles is of a particle size which is suitable for use in a downwardly moving catalyst system or an upflowing fluid catalyst system. The solid thermophore particle may be sized, shaped and composed of the same or a different density material to particularly facilitate movement of the different particle materials concurrently or counter currently as desired and contemplated by the invention. The solid relatively inert and catalyst particles may be sized within the range of 20 or more microns and about 40 microns up to about ¼ inch in diameter. It is preferred to employ the inert particles as the larger sized particle in counter current arrangements.

A general guideline of the ratio of active component to inert solid used in each reactor is useful. Expressed in terms of catalyst alpha activity, a range of 20 to 50 alpha activity based on total volume of solids (i.e., active component plus inert solid) is sufficient for the conversion process contemplated under the specified range of operating conditions. A fresh active catalyst component may have an alpha activity in the range of about 200 to about 2000. In fixed bed prior art operations the active catalyst component is extruded with about 35% binder to form the catalyst particles. The reactor is loaded with 100% catalyst particles. Thus, initially, a large excess of catalyst activity is present. The exothermic reactions initially take place in a very narrow zone or band at the top of the fixed catalyst bed in the reactor space creating heat removal problems. Steam produced in the reactions comprising this invention pass through the rest of the catalyst bed causing catalyst deactivation without ever effectively utilizing its available initial high activity since the reactions are essentially already 100% complete at the time of contact.

In the instant invention, the active catalyst particles are mixed with inert solids such that the alpha activity of the combined solids in the reactor falls in the range of about 20 to about 50. For example, when the active catalyst particles have an alpha activity of 200 a volume ratio of inert solid to catalyst in the range of 4 to 10, (i.e., 4–10 parts of inert to 1 part of catalyst particles) are present in the reactor space. In the absence of excess activity, the reactions take place throughout the reactor, allowing the exothermic heat to be more evenly dissipated. This also reduces the amount of catalyst needed initially for the reactor, and thus substantially reduces if not eliminates undesired steam deactivation of the catalyst.

The activity per reactor volume may be adjusted at anytime if desired by either changing the ratio of inert solid to catalyst, or by changing the activity of the catalyst particles, for example, by adding high activity fresh make-up catalyst from time to time.

By manipulating the catalyst activity and utilization in the manner herein described it is possible to reduce the catalyst requirement of a given reactor system by a factor of 10 or more and thus reduce the cost of the process significantly.

In the various combinations contemplated herein the solid thermophore inert material is a material which acts to limit or exercise some control on the exothermic reaction heat generated, thus it is retained in one or more contact zones for a time consistent with performing as the exothermic temperature control expedient. The inert particles may be caused to move with or counter-current to catayst particles in a given reaction zone either intermittently or continuously. They may move counter-current in a riser fluid catalyst system (FCC type) or concurrent with the catalyst particle material in a downwardly moving catalyst system such as a TCC type of operation. In a more particular aspect the present invention is concerned with effecting exothermic chemical reactions in a catalyst system comprising heat distributing inert particles having the property of absorbing sensible heat in a heat generating reaction zone. As indicated above, the ratio of catalyst particles to heat absorbing inert particles is varied as a function of the catalyst activity and in an arrangement to particularly limit undesired exposure of the catalyst downstream of the reaction front to deactivation of catalyst particles by reaction product such as promoted by steam, a necessary product of the exothermic reaction.

The present invention is particularly concerned with controlling exothermic reactions such as the conversion of methanol and related low boiling alcohols to gasoline boiling components by contacting the alcohol reactant charge or derivatives thereof with a particular class of crystalline zeolites having the property of forming carbon-hydrogen fragments which are oligomerized, isomerized and cyclized to form products having 90% boiling point not substantially above about 400° F. and boiling primarily in the gasoline boiling range. The chemical reactions promoted by the combination operation of this invention are promoted at temperatures selected from within the range of 550° to 1000° F.; pressures within the range of 1 to 30 atmospheres; and a space velocity selected from within the range of 0.5 to 50 LHSV. In accordance with this invention the operating conditions are modified as the activity of the catalyst changes with use. Thus, the reaction operating severity may be modified when using the highest activity catalyst by using a much lower temperature operation in combination with a relatively small amount of the high activity catalyst particles in combination with the relatively inert particles during on stream operation. The catalyst activity is reduced through use to a lower controlled level by the method of this invention and thereafter the temperature of the catalytic operation and concentration of catalyst particles with respect to inert particles may be increased to a level particularly promoting the chemical reactions desired. Thus, the control mechanisms of this invention depend upon catalyst activity, distribution and adsorption of generated heat, dispersal of the reaction front, a concentration of catalyst particles on an activity parameter to achieve conversions of desired severity and a generally precise control upon each of these parameters influenced substantially by the use of relatively inert heat absorbing solid particle material in the catalyst system.

The concepts of this invention contemplate the use of a single reaction zone or a plurality of suitably connected reaction zones arranged to accomplish the reaction parameters above-described. Thus, in one embodiment the concentration of catalyst particles and inert heat absorbing particles may be varied in a single reaction zone or in a plurality of sequentially arranged catalyst contact zones. The sequentially arranged contact zones being provided for effecting cascade of catalyst particles from one zone to another after the catalyst has attained a lower level of activity. Thus, in the plural reactor system each reactor of the system may be provided with an arrangement for effecting separation of inert particles from catalyst and recycle of one or both so that catalyst particles separated from reactant product may be recycled to the reactor from which obtained until the catalyst activity has attained a desired lower limit sufficient for use in another reactor system under conditions of higher catalyst concentration and higher reaction temperature. It is contemplated, for example, of maintainng or restricting the catalyst activity in a first contact zone restricted to within the range of 150 to 1000 alpha activity and the catalyst activity in a downstream reaction zone restricted to within the range of 20 to 50 alpha activity. Of course, more than two sequentially arranged contact zones may be employed with the highest activity and the catalyst activity in each zone appropriately distributed to achieve the results desired particularly with respect to reaction front.

In the environment of exothermic chemical reactions contemplated by this invention the catalyst particles are coke deactivated relatively slowly but steam deactivated much more rapidly. Thus, in any fixed bed catalyst operation of the prior art, the portion of the catalyst bed downstream of the reaction front is substantially deactivated by process formed steam as the reaction front moves through the catalyst bed. This substantial catalyst deactivation occurs before the catalyst in the downstream portion of the fixed bed of catalyst can be used at its highest activity to effect the chemical reactions desired. In a fixed bed catalyst operation it is known that the mass of catalyst is not efficiently and effectively used in its highest activity condition since the reaction front moves in a relatively thin layer through the fixed mass of catalyst continuously exposed to decreasing activity conditions. A moving catalyst system, on the other hand, substantially obviates this undesired downstram catalytic deactivating phenomenon particularly promoted by product steam and observed with the fixed bed catalyst operations. In a moving dispersed phase catalyst system herein contemplated the amount of catalyst in contact with the reactant and product thereof is more effectively distributed. Thus, substantially as rapidly as the desired reaction occurs and a desired product is formed, the generated heat is absorbed, the catalyst is separated from the reaction products and the deactivation effects of process conditions and products are thereby substantially reduced to a bare minimum.

The concepts of the present invention include monitoring and controlling the activity of any given mass of zeolite catalyst employed so that its activity per unit volume of reactor space is maintained nearly constant throughout the length of the reaction path in the reaction zone employed and then substantially immediately separated. Thus, in one of the moving catalyst systems comprising this invention, the activity of the catalyst mass for converting methanol to gasoline boiling products is effectively controlled by mixing a selected quantity of the zeolite catalyst component with the relatively inert solid component preferably of physical characteristics making it easily separated from the zeolite catalyst component. In one particular embodiment it is contemplated accomplishing the above by employing a relatively large mass of inert solid particles in a reaction zone in admixture with an amount of high activity crystalline zeolite being retained in or passed through the void space provided by the inert particles to thereby limit the reactant - catalyst contact time in the reaction zone. It is preferred in such an arrangement that the catalyst particles be of a fluidizable particle size which pass with the reactant material through the void space provided and counter current to the flow of inert particles and then rapidly separate reactant product from catalysts after limited contact time. After the zeolite catalyst is deactivated to a pre-selected level the mass of the less active zeolite catalyst is increased with respect to the inert particles and contacted with reactant to maintain a desired conversion. This may be accomplished by reducing the concentration of inert particles in a single reaction system or the catalyst may be cascaded to another reaction zone containing a larger mass of the less active catalyst. In such a multiple reactor arrangement, it is proposed in one arrangement to operate each reaction zone as a separate moving or fluid catalyst contact zone comprising heat distributing discrete particle material and providing separation of catalyst particles from reactant product very rapidly following traverse of each reaction zone. The separated particles of catalyst and inert solids may be recycled separately to the reaction zone from which it is derived after temperature adjustment of each until such time that the catalyst activity is reduced sufficiently to transfer the less active catalyst particles to a larger mass of catalyst in another zone or to a catalyst regeneration zone. Thus in any one arrangement of reaction zones, the mass of inert and catalyst particles may be caused to flow concurrent or counter current to one another so that the inert particles may flow through a separate cooling zone as required before return to the reaction zone. On the other hand, the inert particles may be retained in a single reaction zone throughout a predetermined catalyst activity decline and thereafter partially removed to reduce the mass of inerts with respect to the mass of the less active zeolite catalyst. In anyone of the catalyst systems utilizing the concepts of this invention fresh make-up catalyst is needed only to compensate for a loss of the highest activity catalyst particles. In the catalyst systems involving a sequence of reaction zones it is not essential that the reaction zones be of the same size. For example, the highest activity zeolite catalyst conversion zone may be a relatively small fluid bed catalyst reaction zone or it may be for example a riser reaction zone with up-flow of catalyst fines through channels and void space provided by retained or downflowing inert solids. The zeolite catalyst conversion zone of reduced activity may be a larger contact zone or it may be the same size as the most active catalyst contact zone but contain a smaller amount of inert solids through which the catalyst reactant mixture passes.

The essence of the present invention is effectively pursued by effecting the exothermic conversion of methanol or companion boiling alcohols and derivatives thereof with a fluid particulate of crystalline zeolite catalyst providing a pore dimension greater than about 5 Angstroms, a pore window of a size provided by 10 membered rings of oxygen atoms, a silica to alumina ratio of at least 12 and a constraint index in the range of 1 to 12.

The catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina rations, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered ring oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to given an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| TMA Offretite | 3.7 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar material. Recently issued U.S. Pat. No. 3,702,886 describing and claimed ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. Application, Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two different zeolites, one or both of which are the effective material insofar as the catalysis of this invention is concerned. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F. for from about 15 minutes to about 24 hours.

Natural zeolites may sometimes be converted to the type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12; a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference of Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the preview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

DISCUSSION OF SPECIFIC EMBODIMENTS

FIG. I is a diagrammatic sketch in elevation of an arrangement of apparatus providing concurrent flow of catalyst and inert solid particles for effecting the exothermic conversion of aliphatic hetero-compounds to gasoline boiling hydrocarbons.

FIG. II is a diagrammatic sketch in elevation of an arrangement of apparatus for practicing a counter current flow of catalyst and reactant with respect to inert heat absorbing solids in a plural arrangement of contact zones providing cascade of catalyst from one zone to another to compensate for changes in the catalyst activity during the conversion operations.

Referring now to FIG. I there is shown a catalyst-inert solids mixing zone 2, a reactor zone 4, a catalyst-inert solids classifier zone 6 and a catalyst regeneration zone 8. In zone 2, a desired ratio of inert solids and catalyst particles is formed for passage by conduit 10 to the reactor zone 4 and concurrent downward flow of the solids therethrough. An alcohol reactant material and/or ether derivative thereof is introduced to the lower portion of zone 4 by conduits 12 and 14 for flow upwardly through the zone and counter current to the flowing particle material. Products of reaction are withdrawn by conduit 16. In the event that catalyst fines are entrained with the product, the product in conduit 16 is passed to suitable cyclonic separating equipment to obtain separation of catalyst particles from reaction product. The separated catalyst particles may be returned to the system as desired, either before or after regeneration. The reactant product thus recovered is thereafter passed to product recovery equipment not shown wherein gasoline boiling hydrocarbons are particularly recovered.

The mixture of catalyst and inert solids passing downwardly through reaction zone 4 is withdrawn by conduit 18 for passage to a classifer 6 diagrammatically shown in the arrangement of FIG. I. The larger black dots shown in the reaction zone 4 are intended to represent inert heat absorbing solid particulate material and the smaller dots there between are intended to identify catalyst particulate material. The large inert particles charged to classifier 6 are retained on the top side of sloping grate 20 and are withdrawn therefrom separate from catalyst particles by conduit 22 provided with a flow control valve. The catalyst particles of smaller particle size pass through sloping grate 20 and are withdrawn therefrom by either conduit 24 or conduit 26 as desired with each being provided with suitable flow control valves. For example, when the catalyst loses activity due to deposition of the coke and requires regeneration it is withdrawn by conduit 26 and passed to a catalyst regeneration zone 8 wherein carbonaceous material is removed by burning in an oxygen atmosphere. The regenerated catalyst is withdrawn from the regeneration zone by conduit 28 containing a flow control valve for passage to a transport conduit 30. The catalyst introduced to transport conduit 30 is conveyed with relatively inert lift gas introduced by conduit 32 to mixing zone 2. In the event that the catalyst does not require regeneration it is withdrawn by conduit 24 and passed to transport conduit 30 for conveyance with inert lift gas to mixing zone 2.

The inert solids withdrawn from classifier 6 by conduit 22 pass to a separate transport conduit 34 provided with lift gas introduced by conduit 36. The lift gas employed by either conduit 32 or 36 may be of a temperature which will effect a partial and desired cooling of solids during transport through conduits 30 and 34. The lift gas may be substantially any suitable relatively inert gaseous stream available for the purpose. The lift gas employed in the transport conduits is separated from solids in mixing zone 2 and withdrawn therefrom substantially free of solids by conduit 38. The contact zones above identified are maintained under processing conditions which will particularly restrict the reaction conversion conditions in zone 4 within the limits expressed hereinbefore.

In the arrangement of FIG. II, the catalyst particles and inert particles are maintained in counter current flow arrangement to one another in one or more of the reaction zones as required to distribute the exothermic heat of reaction. In the arrangement of FIG. II the catalyst particles are caused to flow upwardly through the void space provided between inert particles with the rate of withdrawal of inert particles being relatively slow or intermittent.

In the arrangement of FIG. II a reactant feed comprising a lower alcohol such as methanol and/or an ether derivatives thereof is introduced to the processing steps by conduit 40 for commingling of recycled catalyst in conduit 44 with or without the addition of fresh make-up catalyst by conduit 42. A suspension is thus formed between reactant and catalyst particles under conditions providing an initiating reaction temperature within the limits hereinbefore discussed. The suspension thus formed is passed upwardly through the void space provided between the relatively inert heat distributing particles 46 which generally are of a larger particle size than the catalyst particles retained in zone 48. As indicated hereinbefore, the concentration of inert solids 46 in the high activity catalyst reaction zone is of a higher concentration of particles than is employed in another zone wherein the catalyst activity is a lower order of magnitude. In any one of these arrangements the inert solids may be intermittently or continuously removed from the reaction zone. Conduits 50 and 52 are provided for introducing and withdrawing inert solids from zone 48.

The products of methanol conversion with entrained zeolite catalyst pass from the reaction zone by conduit 54 to a cyclonic separation zone 56 wherein catalyst is separated from reaction products and then removed by conduit 58. The catalyst thus separated is collected in a bottom portion of separation zone 56 for withdrawal and recycle by conduit 44 provided with a flow control valve. On the other hand, the catalyst separated in zone 56 may be cascaded by conduit 60 to a separate reaction zone 62 wherein a mass of lower activity catalyst particles is particularly retained for effecting the conversion operation herein described. The transfer of catalyst by conduit 60 occurs after a pre-determined loss in catalyst activity. The catalyst recycle or transfer to zone 62 is contacted with a reactant material such as a lower alcohol comprising methanol or an ether derivative thereof introduced by conduit 64. A catalyst reactant suspension mixture is formed and passed upwardly through zone 62 and through the void space provided between inert heat absorbing particles 66 maintained in reaction zone 62. The inert particles may be moved continuously or intermittently through zone 62 and conduits 68 and 70 are provided for accomplishing this purpose. The inert particles withdrawn from either zone 48 or 62 may be regenerated and/or cooled prior to return to the reaction zone in equipment not shown.

The products of reaction and suspended catalyst passed upwardly through zone 62 pass through an upper portion thereof by conduit 72 to cyclonic separating equipment 74 wherein a separation is made between catalyst particles and reaction products. The reaction products are recovered by conduit 76 and further separated as desired to recover gasoline boiling components. The catalyst separated in zone 74 is collected in the bottom portion thereof and withdrawn by conduit 78 communicating with conduit 60. It is contemplated, however, in the operating concept of this invention that all or a portion of the separated catalyst in zone 74 may be withdrawn by conduit 80 for passage to a catalyst regeneration operation not shown. Regenerated catalyst may then be passed to one or both of the reaction zones as by either conduit 42 or conduit 82.

The operating conditions employed in the respective zones above described are maintained within the limits particularly discussed hereinbefore to accomplish the conversion of lower alcohols and/or ether derivatives thereof to gasoline boiling range hydrocarbons.

Having thus generally described the invention and discussed specific operating embodiments going to the very essence thereof, it is to be understood that no undue restrictions are to be imposed by reasons thereof except as defined by the following claims.

I claim:

1. In a process for effecting exothermic vapor phase chemical reactions of reactants comprising methanol, companion low boiling alcohols and derivatives thereof to form gasoline boiling hydrocarbons with a crystalline zeolite catalyst characterized by a pore opening of at least 5 Angstroms, a silica-alumina ratio of at least 12, and a constraint index within the range of 1 to 12 wherein in a fixed catalyst bed operation, the catalyst downstream of the reaction front becomes deactivated by a reaction product component, thereby substantially reducing utilization of the catalyst mass at its introduced activity to effect said exothermic reactions, the improvement to particularly limit undesired exposure of the catalyst downstream of the reaction front to deactivation by a reaction product which comprises, passing the chemical reactants in vapor phase with said zeolite catalyst through a reaction zone containing a mixture of active catalyst particles and inert solid particle diluent thermophore material, the mass of active catalyst particles admixed with solid inert diluent thermophore material in a reaction zone being proportioned with respect to one another for any given and selected catalyst alpha activity in the range of 20 to 1000 alpha to more effectively utilize the particular alpha activity of the catalyst as the desired reaction front and catalyst pass through the reaction zone and effecting the reaction in the absence of significant undesired exposure of the active catalyst particles downstream of the reaction front to deactivating product of reaction before separation of catalyst from reaction products.

2. The process of claim 1 wherein the inert particle moves generally counter current to the catalyst particle.

3. The process of claim 1 wherein the inert particle moves generally concurrent with the catalyst particles.

4. The process of claim 1 wherein the inert particle passes through a reaction zone at a different rate than said catalyst particle.

5. The process of claim 1 wherein the inert heat absorbing thermophore particle is relied upon as an exothermic temperature control expedient in the reaction zone.

6. The process of claim 1 wherein the exothermic chemical reaction is effected in a plurality of separate reaction zones and a downstream reaction zone utilizes catalyst providing an alpha activity within the range of 20 to 50.

7. The process of claim 1 wherein the catalyst utilized in any given reaction zone is continuously passed therethrough and recycled thereto and utilized until its activity is reduced a predetermined amount and then the catalyst reduced to a selected lower activity is passed to another reaction zone.

8. The process of claim 1 wherein the amount of inert particles retained in any given reaction zone is changed as the alpha activity of the catalyst retained in a reaction zone is reduced to a lower level.

9. The process of claim 1 wherein catalyst particles and inert particles each pass through a given reaction zone and the inert particles are cooled before return to the reaction zone.

* * * * *

UNITED STATES PATENT AND TRADEMARK OFFICE
CERTIFICATE OF CORRECTION

PATENT NO. : 4,118,431
DATED : October 3, 1978
INVENTOR(S) : Nai Yuen Chen

It is certified that error appears in the above-identified patent and that said Letters Patent are hereby corrected as shown below:

Col. 1, Line 22   "absorb" should be "adsorb"
Col. 5, Line 30   "boiling" should be "low boiling"
Col. 8, Line 18   after "and", insert "ZSM-21, with"

Signed and Sealed this

Thirteenth Day of February 1979

[SEAL]

Attest:

RUTH C. MASON
Attesting Officer

DONALD W. BANNER
Commissioner of Patents and Trademarks